US006761689B2

(12) United States Patent
Salgo et al.

(10) Patent No.: US 6,761,689 B2
(45) Date of Patent: Jul. 13, 2004

(54) BIPLANE ULTRASONIC IMAGING

(75) Inventors: Ivan Salgo, Andover, MA (US);
Douglas Demers, Haverhill, MA (US);
Mark Ward, Methuen, MA (US);
Janice Frisa, Atkinson, NH (US);
McKee Dunn Poland, Andover, MA (US); Bernard Savord, Andover, MA (US); Paul Detmer, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/286,664

(22) Filed: Oct. 31, 2002

(65) Prior Publication Data

US 2003/0060710 A1 Mar. 27, 2003

Related U.S. Application Data

(63) Continuation-in-part of application No. 10/231,704, filed on Aug. 29, 2002, which is a continuation-in-part of application No. 09/641,306, filed on Aug. 17, 2000, now Pat. No. 6,443,896.

(51) Int. Cl.[7] ............................................. A61B 8/02
(52) U.S. Cl. ............................................... 600/447
(58) Field of Search ................................ 600/443, 447, 600/459, 437; 73/606, 602, 625, 628; 367/7, 11; 345/419

(56) References Cited

U.S. PATENT DOCUMENTS

| 5,050,610 | A |   | 9/1991  | Oaks et al. |
| 5,207,225 | A | * | 5/1993  | Oaks et al. ............... 600/443 |
| 5,353,354 | A |   | 10/1994 | Keller et al. |
| 5,454,371 | A | * | 10/1995 | Fenster et al. ............... 600/443 |
| 5,546,807 | A | * | 8/1996  | Oxaal et al. .................. 73/606 |
| 5,608,849 | A | * | 3/1997  | King, Jr. ..................... 345/419 |
| 5,876,345 | A |   | 3/1999  | Eaton et al. |
| 6,099,474 | A | * | 8/2000  | Solek ......................... 600/459 |
| 6,241,675 | B1 | * | 6/2001 | Smith et al. ................. 600/443 |
| 6,245,017 | B1 | * | 6/2001 | Hashimoto et al. ......... 600/447 |
| 6,276,211 | B1 |   | 8/2001 | Smith |
| 6,413,219 | B1 | * | 7/2002 | Avila et al. ................. 600/443 |
| 6,443,896 | B1 |   | 9/2002 | Detmer |
| 6,447,454 | B1 |   | 9/2002 | Chenal et al. |

FOREIGN PATENT DOCUMENTS

| DE | 198 54 241 A | 6/2000 |
| WO | WO 00/58754 A | 10/2000 |

OTHER PUBLICATIONS

Snyder, et al., "Real–Time Orthogonal Mode Scanning of the Heart.I. System Design," JACC vol. 7, No. 6, Jun. 1986, pp. 1279–1285.

* cited by examiner

*Primary Examiner*—Mary Beth Jones
*Assistant Examiner*—Ruby Jain
(74) *Attorney, Agent, or Firm*—W. Brinton Yorks, Jr.

(57) ABSTRACT

An ultrasonic apparatus and method are described in which a volumetric region of the body is imaged by biplane images. One biplane image has a fixed planar orientation to the transducer, and the plane of the other biplane image can be varied in relation to the fixed reference image. In a preferred embodiment one image can be rotated relative to the other, and can be tilted relative to the other. An image orientation icon is shown on the display screen together with the two biplane images depicting the relative orientation of the two planar images.

17 Claims, 7 Drawing Sheets

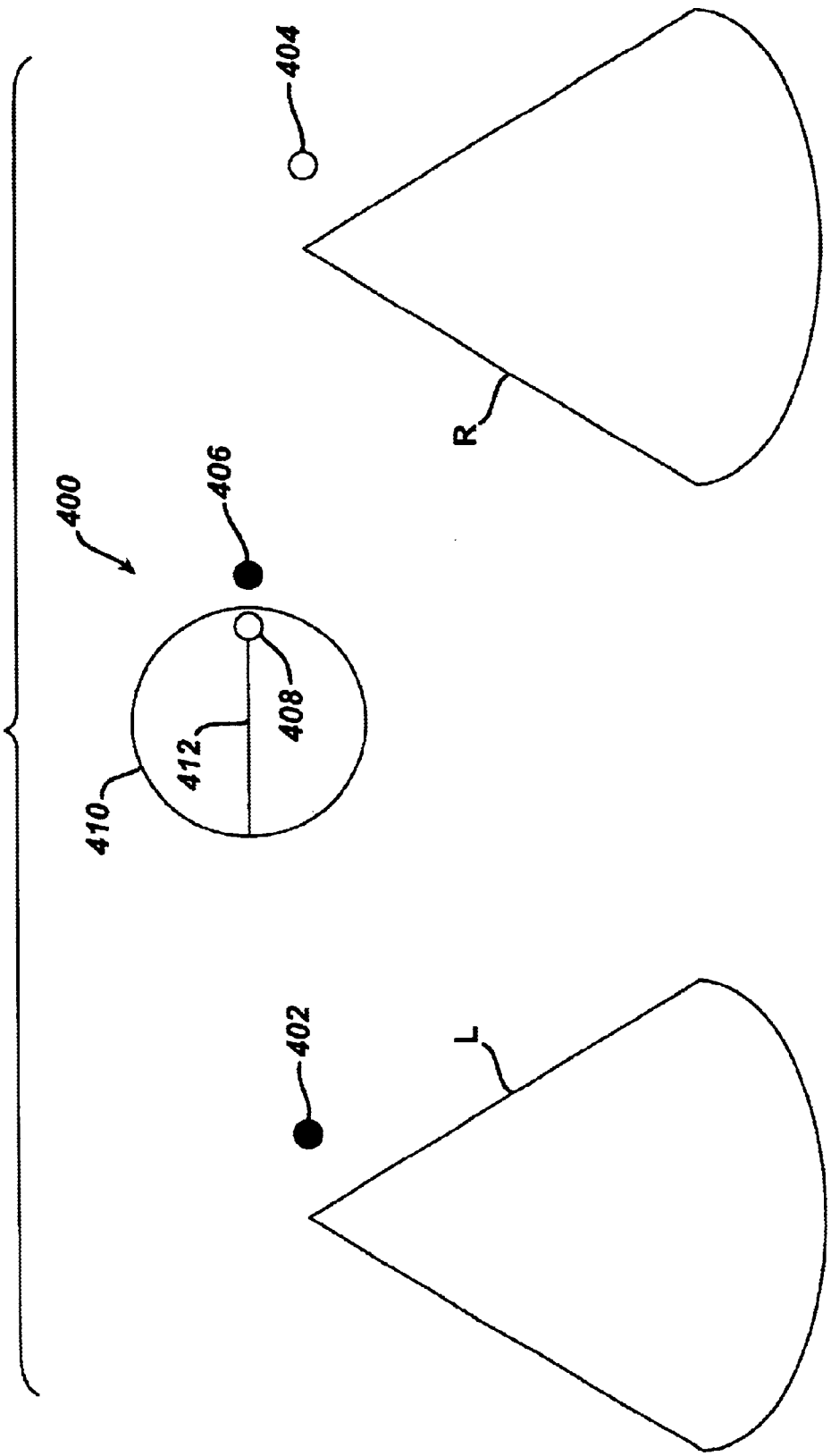

30

210

210

30

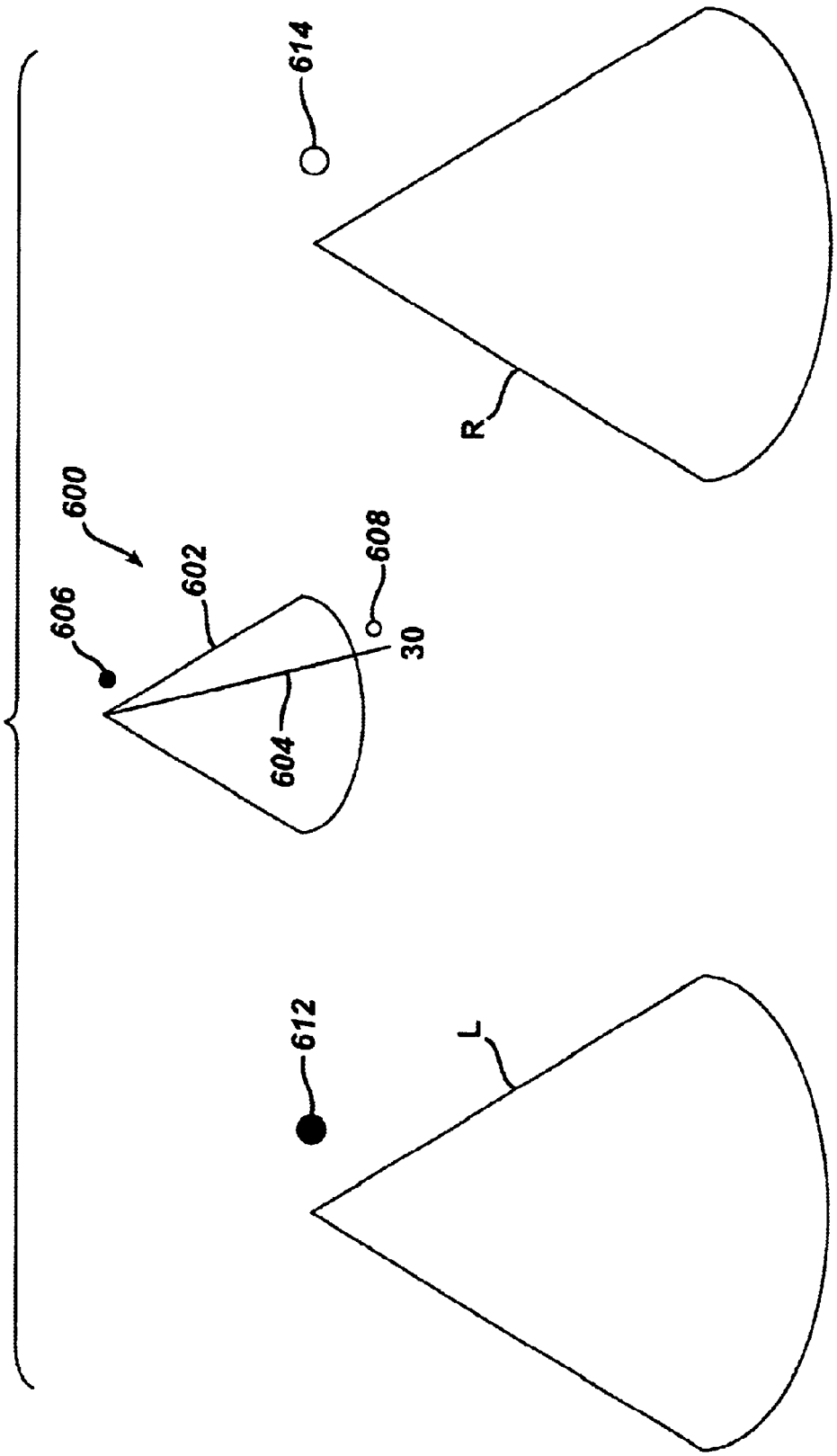

BIPLANE ULTRASONIC IMAGING

RELATED APPLICATION

This is a divisional application of U.S. patent application Ser. No. 10/231,704, filed Aug. 29, 2002, which is a continuation in part application of U.S. patent application Ser. No. 09/641,306, filed Aug. 17, 2000 and now U.S. Pat. No. 6,443,896.

TECHNICAL FIELD

This invention relates generally to ultrasonic imaging and, more particularly, to creating multiple planar ultrasonic images of a volumetric region of the body in real-time.

BACKGROUND

A major advantage of three-dimensional ultrasonic imaging is the ability it provides to obtain unique image planes through the volume of an object such as a human body, image planes not available through conventional two-dimensional scanning. For example, through three-dimensional imaging techniques one can look simultaneously at several different cut planes of a region of tissue to thereby observe features from different angles or views. Alternatively, it may be desirable in certain instances, to view an image plane at a constant depth below the object surface such as the skin; such an image plane cannot be obtained with normal two-dimensional scanning because of the orientation of the ultrasonic probe relative to the object.

With the ability to acquire multiple image planes of a volumetric region comes the need to define the planes to be imaged, their relationship to each other in space, and the best way to display the images. In the past, a common display technique has been to display three ultrasound images of a volumetric region which are of mutually orthogonal planes. Each image has two orthogonal cross-hairs displayed over it, depicting the positions of the other two orthogonal image planes. As the cross-hairs are dragged to different positions, a new parallel image plane in that dimension is selected and displayed. This display technique enables the clinician to survey and define tissue structures in a volumetric region by their appearances in intersecting image planes.

Such a display is useful for static image data of a volumetric region, which can readily be appropriately readdressed for display of different image planes as the selection cross-hairs are moved. The display technique does not lend itself to real-time imaging, as the complexity of control and display would be increased significantly for real-time imaging. Furthermore, such a real-time display can present too much information for the clinician to analyze in a methodical or organized manner. Hence there is a need for effective display and control of multiple real-time planar images of a volumetric region.

SUMMARY OF THE INVENTION

In accordance with the principles of the present invention, method and apparatus are describe for creating and displaying multiple planar images of a volumetric region of the body. In one aspect of the invention, two real-time image planes are acquired and displayed in what is referred to herein as a "biplane" display format. The two planes of the biplane display can be controlled in two control modes, one in which one image plane is tilted relative to the other, and another in which one image plane is rotated relative to the other. In another aspect of the invention, an icon is displayed concurrently with the biplane images to inform the clinician as to the relative orientation of the two image planes.

BRIEF DESCRIPTION OF THE DRAWINGS

FIG. 4 illustrates a biplane display when operating in the "rotate" mode.

FIG. 6 illustrates a biplane display when operating in the "tilt" mode.

DETAILED DESCRIPTION

Figure 1:
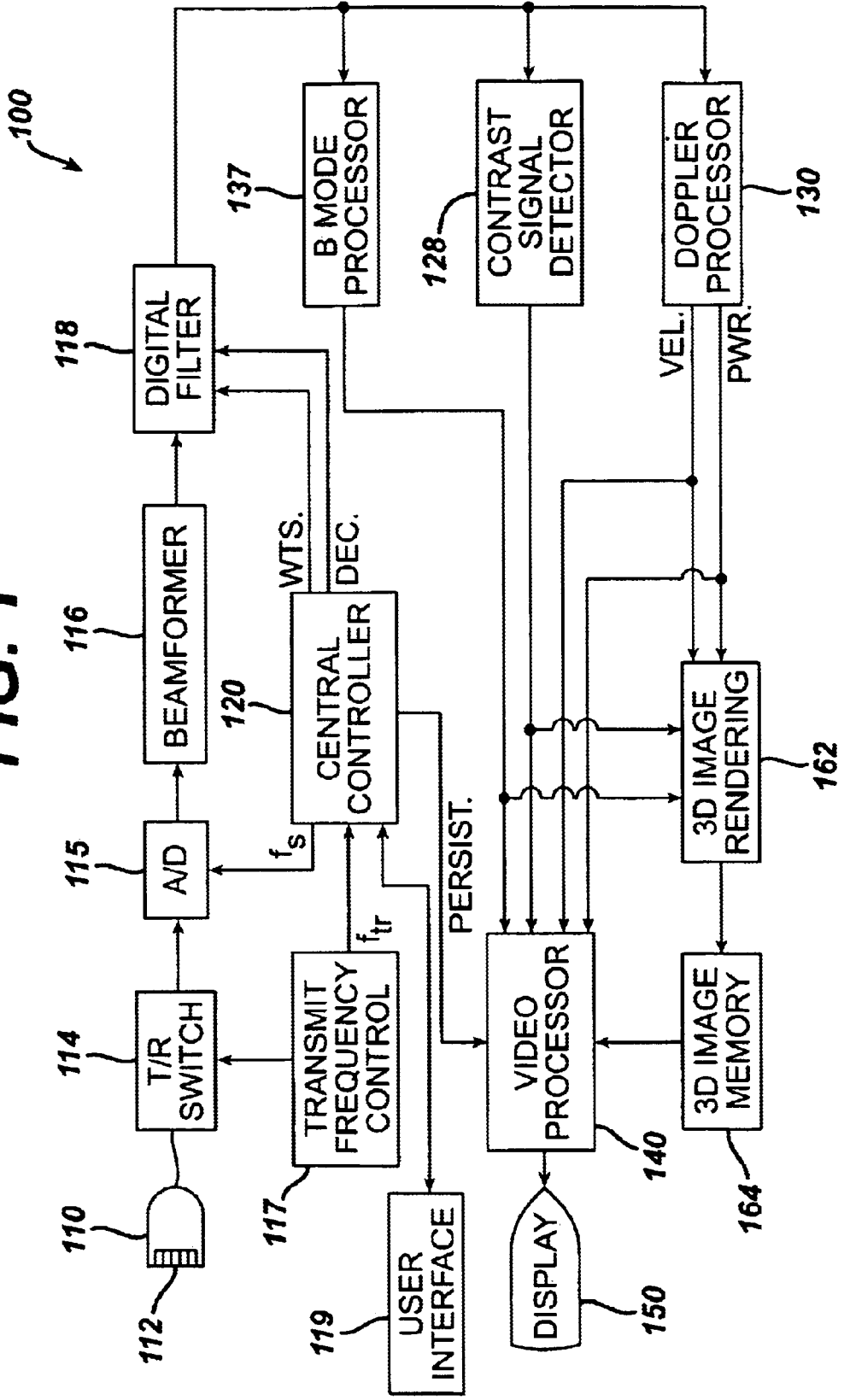
FIG. 1 is a block diagram of an ultrasonic diagnostic imaging system constructed in accordance with the principles of the present invention.

FIG. 1 is a block diagram of an ultrasonic diagnostic imaging system 100 with which methods and apparatus in accordance with the invention can be used. It should be understood that the invention is not limited to use with this imaging system but is shown implemented therein only as an example. In the imaging system 100, a central controller 120 commands a transmit frequency control 117 to transmit a desired transmit frequency band. The parameters of the transmit frequency band, $f_{tr}$, are coupled to the transmit frequency control 117, which causes a transducer 112 of an ultrasonic probe 110 to transmit ultrasonic waves in the selected frequency band. It will be understood, of course, that any ultrasonic frequency or group of frequencies, known as a frequency signature, may be used, with due consideration of the desired depth of penetration and the sensitivity of the transducer and ultrasonic system. The transducer 112 of the probe 110 comprises an array of discrete elements that transmit ultrasonic energy in the form of a beam, and receive echo signals returned in response to this transmission. The beam can be steered to scan different parts of an object by mechanically moving the probe or, preferably, by electronically adjusting the timing of the transmission for the various array elements. In image system 100, this steering is controlled by central controller 120. The controller 120, in turn, responds to commands from a user entered via a user interface 119 that includes an interface program and a pointing device (such as a mouse, trackball, stylus, tablet, touch screen or other pointing device), keyboard, or other input device for conveying instructions to the central controller. Alternatively, the controller may be programmed to steer the beam automatically in a predetermined, default manner. The received signals are coupled through a transmit/receive (T/R) switch 114 and digitized by an analog-to-digital converter 115. The sampling frequency $f_s$ of the A/D converter is controlled by the central controller 120. The desired sampling rate dictated by sampling theory is at least twice the highest frequency $f_c$ of the received echoes. Sampling rates higher than the minimum requirement can also be used. The signal samples are delayed and summed by a beam former 116 to form coherent echo signals. The coherent echo signals are then filtered by a digital filter 118 to a desired passband. The digital filter 118 can also shift the frequency band to a lower or baseband frequency range. The characteristics of the digital filter are controlled by the central controller 120, which provides the filter with multiplier weights and decimation control. Preferably the arrangement is controlled to operate as a finite impulse response (FIR) filter, and performs both filtering and decimation. A wide range of filter characteristics is possible through programming of the weighting and decimation rates of the filter, under control of the central controller 120. The use of a digital filter allows the advantage of flexibility in providing different filter characteristics. A digital filter can be programmed to pass received fundamental frequencies at one moment, and harmonic frequencies at the next. The digital filter can thus be operated to alternately produce images or lines of fundamental and harmonic digital signals, or lines of different alternating harmonics in a time-interleaved sequence, simply by changing the filter coefficients during signal processing.

From the digital filter 118, the filtered echo signals are detected and processed by a B mode processor 137, a contrast signal detector 128, or a Doppler processor 130. The B mode processor performs functions that include, but are not limited to, frequency compounding, spatial compounding, harmonic image formation, and other typical B mode functions that are well known in the art. The Doppler processor applies conventional Doppler processing to the echo signals to produce velocity and power Doppler signals. The outputs of the processors 137 and 130 and contrast signal detector 128 are coupled to a video processor 140 for display as a two-dimensional ultrasonic image on the display 150. The central controller 120 keeps track of the sequence of the incoming signals, and so enables the video processor 140 to place the current data in the forming image. As signals are received by the video processor 140, the data is fed to the display, producing rasterized images. The outputs of the two processors and contrast signal detector are also coupled to a three-dimensional image rendering processor 162 for the rendering of three-dimensional images, which are stored in a 3D image memory 164 and provided from there to the video processor 140. Three-dimensional rendering may be performed in a conventional manner. With this arrangement, an operator can select among the outputs of the contrast signal detector 128 and the processors 137 and 130 for two- or three-dimensional display of an ultrasonic image.

The system of FIG. 1, through the operation and control of the probe 110, transducer 112, the video processor 140, and/or the image rendering processor 162, provides the ability to create multiple real-time planar images of a volumetric region of an object such as a human body, while the body is being scanned. These planar images, when taken as slices through a body, have known geometric relationships to each other, enabling a diagnostician to view body features from different orientations. The clinician may wish to adjust the relative angles of the slices to visualize spatial relationships of tissue features. Through user interface 119, an operator can adjust the orientation of the slices displayed to align them with the features of interest in the image. Real-time performance is achieved by generating only certain ultrasonic beams needed to construct the desired planar images, rather than the much greater number of beams that would have to be transmitted to scan the entire volumetric region.

Figure 2A:
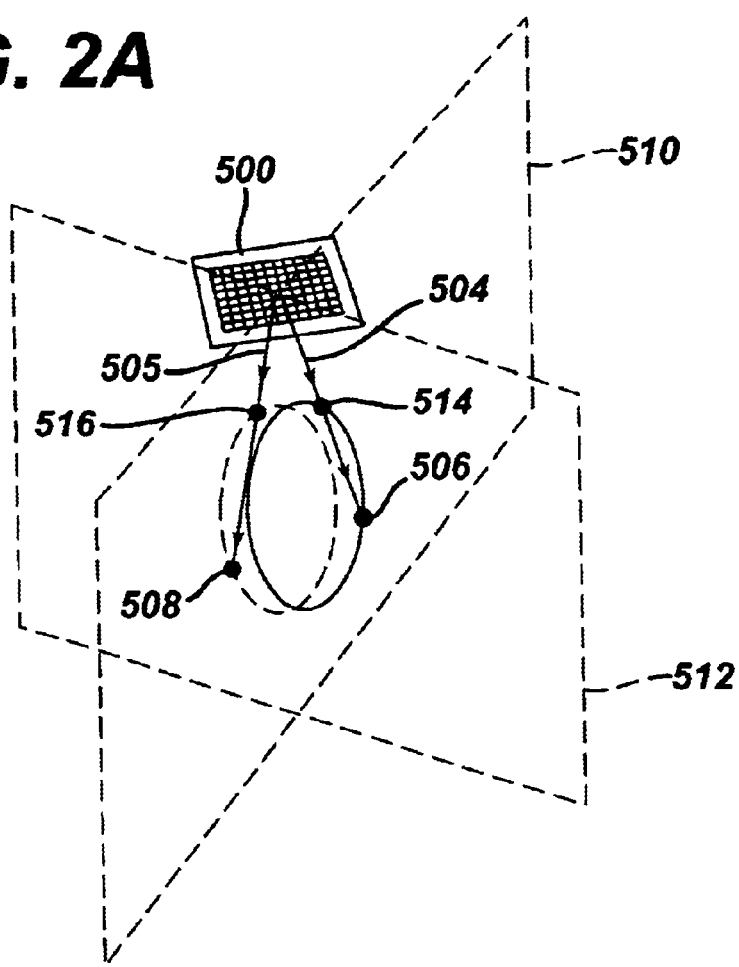
FIGS. 2A and 2B show a display, in real time, of planar images created by use of a two dimensional array transducer with the system of FIG. 1.
Figure 2B:
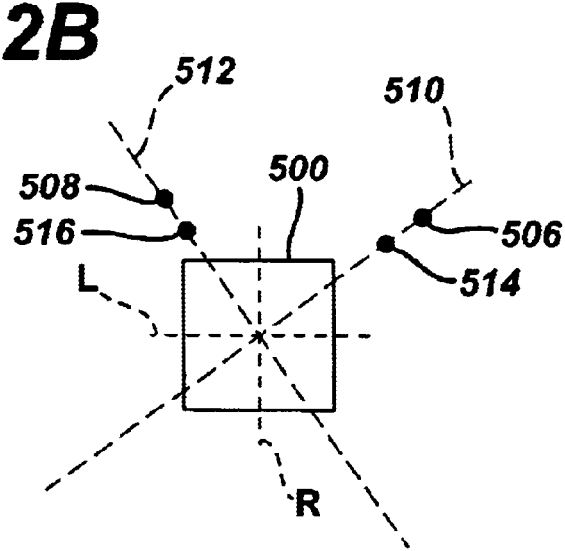

FIGS. 2A and 2B show an embodiment of a transducer 500 that can be used to obtain data from a set of planes 510 and 512. This embodiment generates beams such as beam 504 that lies in plane 510, intersecting points 514 and 506; also beam 505 that lies on plane 512, intersecting points 516 and 508. The rays emanating from two-dimensional array transducer 500 can be electronically steered in three dimensions, thus avoiding the need to mechanically sweep the transducer across the volumetric region of interest. In similar fashion, data is received from the lines of interest in the respective planes using well-known beam steering and focusing and/or gating techniques applicable to a two-dimensional array transducer.

The above scanning method for generating two planar images is preferred because of its speed, but is not exclusive. Variations are possible. If desired, additional beams can be generated which lie in and thereby define additional planes, or intersect additional surfaces. Each additional beam, of course, takes additional time to generate and therefore affects the sweep rate.

The desired number of planes and their orientation is conveyed to central controller 120 through user interface 119. In addition, the transducer 112 can be controlled to emit beams directed toward more than one point in each plane. Alternatively, the transducer can be controlled to emit beams at fewer than all surfaces at each sampling position, as long as the beams lie in at least two planes, or intersect at least two non-planar surfaces, or lie in at least one plane and intersect at least one non-planar surface, per sweep. These and other obvious variations can produce multiple planar images in real-time, but at different rates and with different resolutions, depending on the variation chosen. Furthermore, any two-dimensional ultrasonic imaging technique, for example, B mode, contrast signal detection, harmonic imaging, or Doppler imaging, can be applied equally well with this data acquisition scheme.

Figure 3:
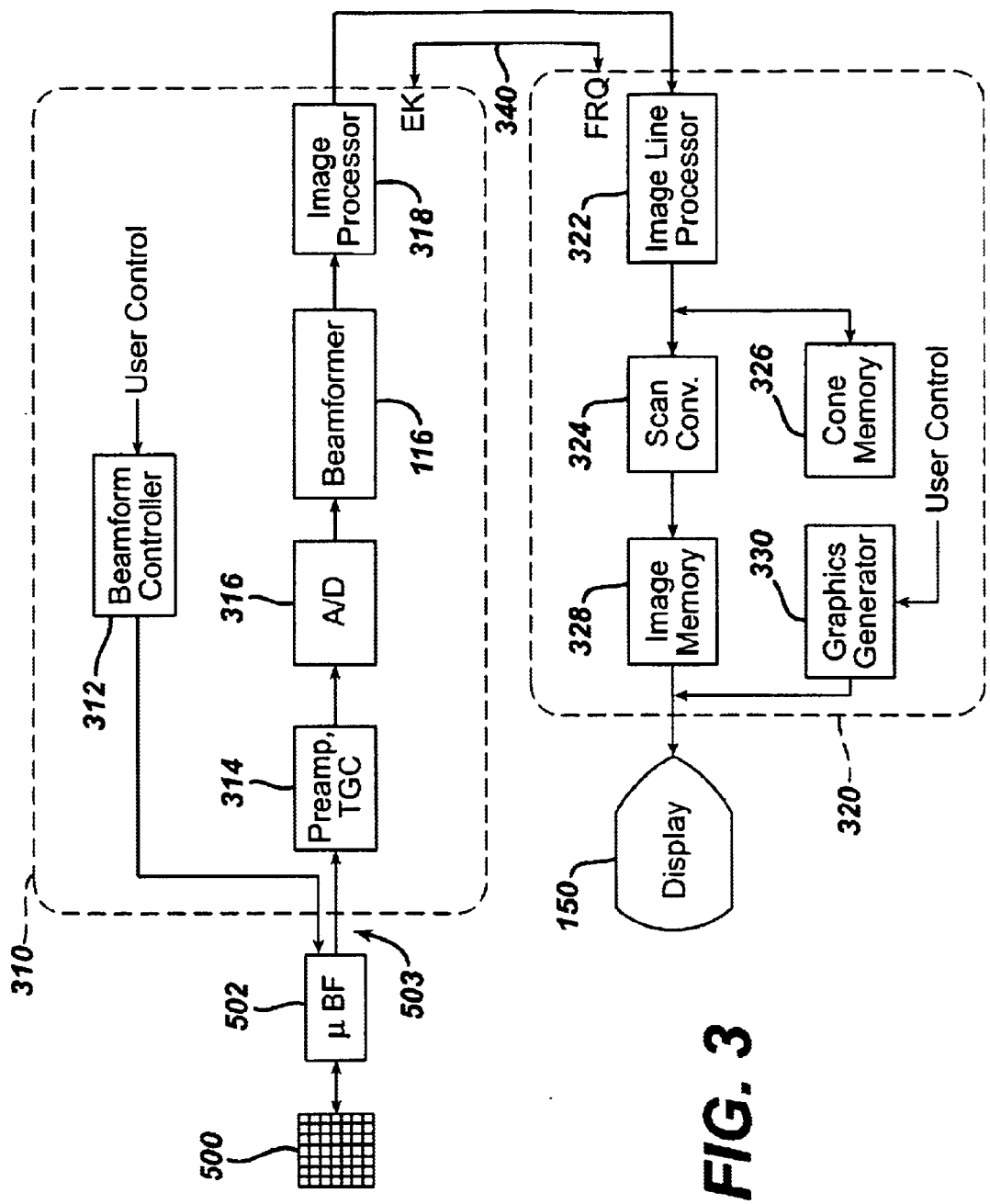
FIG. 3 illustrates in block diagram form a second embodiment of an ultrasonic diagnostic imaging system constructed in accordance with the principles of the present invention.

The data acquired from the two planes 510 and 512 are used by one or more of the processors 137, 130, or the contrast signal detector 128 to construct the corresponding planar images. The planar images are preferably created at a scanning rate to provide real-time imaging. The planar images can be simultaneously displayed side-by-side by the video processor 140, or in a three dimensional perspective view on the display 150 as the volumetric region is continuously scanned, or viewed later. FIG. 3 illustrates another embodiment of an ultrasound system constructed in accordance with the principles of the present invention. In this embodiment the probe 110 includes a two dimensional array transducer 500 and a micro-beamformer 502. The micro-beamformer contains circuitry which control the signals applied to groups of elements ("patches") of the array transducer 500 and does some processing of the echo signals received by elements of each group. Micro-beamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque).

The probe is coupled to the scanner 310 of the ultrasound system. The scanner includes a beamform controller 312 which is responsive to a user control and provides control signals to the microbeamformer 502 instructing the probe as to the timing, frequency, direction and focusing of transmit beams. The beamform controller also controls the beamforming of received echo signals by its coupling to the analog-to-digital (A/D) converters 316 and the beamformer 116. Echo signals received by the probe are amplified by preamplifier and TGC (time gain control) circuitry 314 in the scanner, then digitized by the A/D converters 316. The digitized echo signals are then formed into beams by a beamformer 116. The echo signals are then processed by an image processor 318 which performs digital filtering, B mode detection, and Doppler processing as described above, and can also perform other signal processing such as harmonic separation, speckle reduction through frequency compounding, and other desired image processing.

The echo signals produced by the scanner 310 are coupled to the digital display subsystem 320, which processes the echo signals for display in the desired image format. The echo signals are processed by an image line processor 322, which is capable of sampling the echo signals, splicing segments of beams into complete line signals, and averaging line signals for signal-to-noise improvement or flow persistence. The image lines are scan converted into the desired image format by a scan converter 324 which performs R-theta conversion as is known in the art. The image is then stored in an image memory 328 from which it can be displayed on the display 150. The image in memory is also overlayed with graphics to be displayed with the image, which are generated by a graphics generator 330 which is responsive to a user control. Individual images or image sequences can be stored in a cine memory 326 during capture of image loops.

For real-time volumetric imaging the display subsystem 320 also includes the 3D image rendering processor 162 which receives image lines from the image line processor 322 for the rendering of a real-time three dimensional image which is displayed on the display 150.

In accordance with the principles of the present invention, two images, referred to herein as biplane images, are acquired by the probe in Teal time and displayed in a side by side display format. Since the 2D array 500 has the ability to steer transmitted and received beams in any direction and at any inclination in front of the array, the planes of the biplane image can have any orientation wit respect to the array and to each other, as shown by the orientation of image planes 310, 512 to the array 500 in FIGS. 2A and 28. However in a preferred embodiment the two image planes intersect the center of the array 500 and are orthogonal to the sides of the array as shown by planes L and R in FIG. 2B, in which the planes are viewed "edge-on" from the array transducer. In the examples given below the image format is the sector image format, with the image lines emanating from a near-field apex. However, linear or steered linear scan formats can also be employed.

The biplane images in the two image planes are acquired by transmitting and receiving beams of each image as exemplified by the acquisition of beams 504 and 505 in the respective image planes of FIG. 2A. Various acquisition sequences can be performed. All of the scanlines of one image can be acquired, followed by acquisition of all of the scanlines of the other image. Alternatively, acquisition of the lines of the two images can be time interleaved. For instance, line 1 of one image can be acquired, followed by the acquisition of line 1 of the other image. This would be followed by the acquisition of line 2 of each image, then line 3 of each image, and so forth. This may be advantageous when doing Doppler imaging of low flow velocities, as the interval between interrogations of an ensemble of lines can be lengthened. It also advantageously results in the lines at the intersection of the two planes being acquired in succession, which prevents rapidly moving tissue at the image intersection from appearing different in the two images. The lines can be acquired in their spatial progression in the image, or sequentially from separated portions of the image. For instance, the four edge lines can be acquired first, followed by the four central lines around the intersection of the planes, then progressing alternately toward and away from the intersection.

When all of the lines of both images have been received by the scanner 310 and forwarded to the display subsystem 320, the scanner sends an "EK" signal over control lines 340 to the display subsystem, telling the display subsystem that all of the lines for the current display frame have been sent for display. The display subsystem then processes the image lines for display. For the biplane format described below, one image is processed, formatted and mapped for display on one side of the display screen and the other image is processed, formatted and mapped for display on the other side of the display screen. After the images have been processed the display subsystem returns an "FRQ" control signal to the scanner, informing the scanner that the display subsystem is requesting another image frame for processing. The complete screen display of two side-by-side images is overlaid with the graphics for the images and displayed on the display 150. The display subsystem then awaits the completion of another scanning of the two images as indicated by the concluding receipt of another EK signal, at which time the processing and display of another real time display frame proceeds again.

It is also possible to use a communication architecture in which each image is concluded with an EK signal and the transmission and receipt of both biplane images, each concluded by an EK signal and responded to by an FRQ signal, is done before a two-image display frame is produced by the display subsystem.

Figure 7:
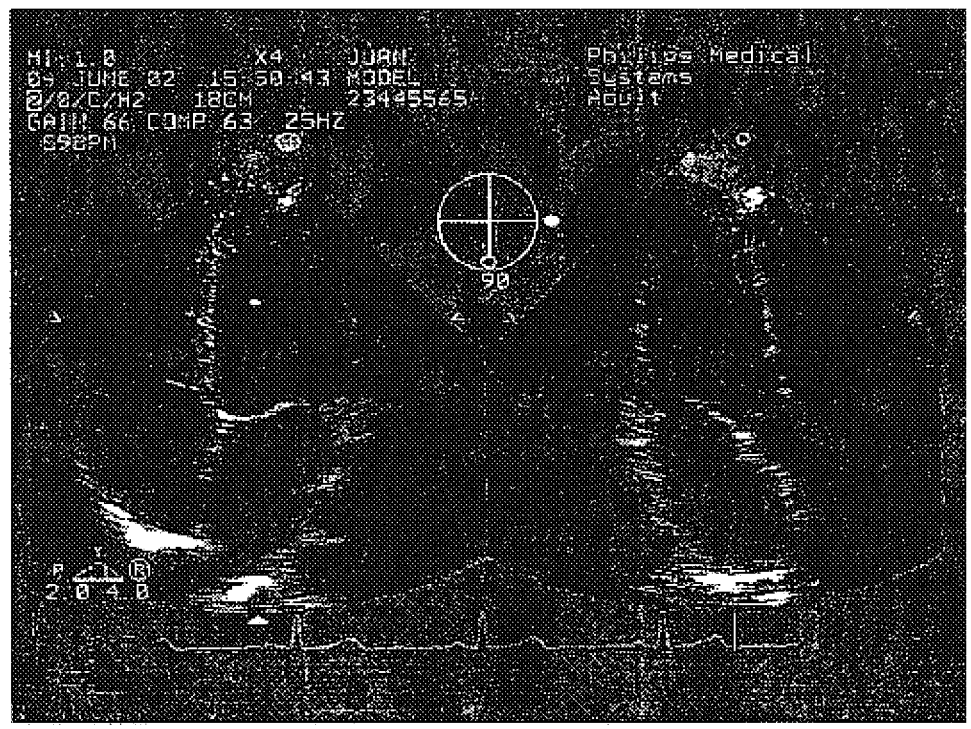
FIG. 7 is a photograph of an actual ultrasound system display when operating in the rotate mode in accordance with the principles of the present invention.

The images are displayed side-by-side as illustrated graphically by images L and R in FIG. 4 and by the photograph of the system display shown in FIG. 7. In a preferred embodiment the image plane orientations are selected by one of two selection modes, "rotate" or "tilt." In a preferred embodiment, the orientation of one image, the left image L in FIG. 4, is fixed in relation to the transducer array. The L image is always in a plane which is orthogonal to the plane of the array, extending through the center of the array as shown in FIG. 2B. The plane of the right image R can be rotated or tilted by user control relative to the plane of image L. In the rotate mode, the two images always share a common center line during sector imaging, and the plane of the right image R can be rotated by manipulation of a user control such as a trackball or knob. The right image can be rotated from being co-planar with the left reference image to a 90° orientation and through to co-planar again. A full 360° of rotation is possible either by manipulation of the user control or by left-to-right inversion of the image. In the tilt mode the center of the right image R always intersects the reference image, but can be tilted to intersect different lines of the reference image as if the sector is swinging from the common apex of the two images.

In a preferred embodiment the probe 110 has a marker on it which identifies a given side of the image. Generally this marker is a physical protrusion or color on one side of the probe case. Clinicians use this marker to relate the orientation of the probe to the orientation of the image on the display. It is customary to display the marker on the display screen as shown by dot 402 in FIG. 4. The clinician will generally always hold the probe with the probe marker in the same position so that the image always is shown with an orientation which the clinician prefers. In accordance with a further aspect of the present invention, the second image R is also shown with an orientation marker 404. In the rotate mode the two images can both be imaging the same plane when scanning is initiated, in which case the markers are spatially aligned. The clinician can then rotate the right image plane from the common starting orientation. In a constructed embodiment the initial condition of the two biplane images is that the two are aligned untilted along a common center line and rotated 90° with respect to each as shown in FIG. 7.

In accordance with a further aspect of the present invention, an icon 400 is displayed on the biplane display to graphically indicate the relative orientation of the two image planes. The icon 400 in FIG. 4 represents a view of the image planes from the transducer array and has a circle 410 which graphically represents the space in which the base of the sector R can rotate. The dot 406 corresponds to the dot 402 of the left reference image L and indicates that the plane of the reference image is in a horizontal orientation across the circle 410 with the marker at the right of the image. The line 412 of the icon indicates that the right image R is in the same orientation with the right image marker 408 (corresponding to dot 404) at the right side of the image.

Figure 5A:
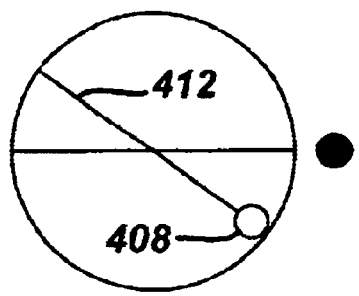
FIGS. 5A–5D illustrate the plane orientation icon of FIG. 4 for different image plane orientations.
Figure 5B:
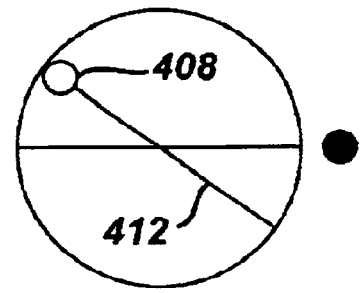

FIGS. 5A–5D illustrate how the icon 400 changes as the right image is rotated. When the right image is rotated 30° from the plane of the reference image, the icon 400 will appear as shown in FIG. 5a, in which the line 412 and dot 408 representing the plane of the right image have rotated thirty degrees. The number 30 also appears below the icon. The right image plane can be rotated another 180°, in which case the line 412 and marker dot 408 will appear as shown in FIG. 5B. The number below the icon changes to 210 to indicate a 210 degree orientation to the reference image plane. Alternatively, in the preferred embodiment the user interface of the ultrasound system includes a "right image invert" control. When this control is actuated, the right image will immediately invert laterally by 180°, and the icon will correspondingly switch from that shown in FIG. 5A to that shown in FIG. 5B.

Figure 5C:
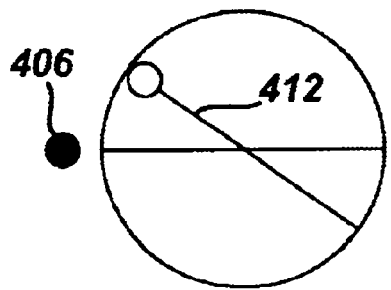
Figure 5D:
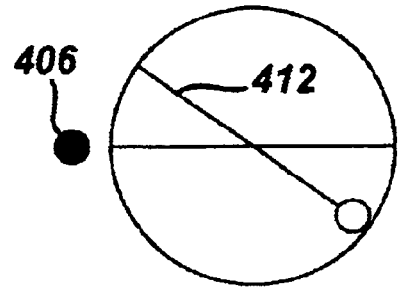

Similarly, the preferred embodiment includes a "left image invert" control which laterally inverts the left image. FIG. 5C illustrates the icon when the reference image has been inverted, in which case the marker dot 406 is at the left side of the icon. In FIG. 5C the right image is at a 210 degree orientation to the original (uninverted) position of the reference image as shown by line 412 and the number below the image. In FIG. 5D the reference image has been inverted with the right image at a 30° orientation to the original position of the left reference image.

An advantage of the common display of the biplane images and the icon is that when the images on the display screen are saved, the icon is also saved without further effort by the sonographer. During later review of the images by a clinician the orientation of the two image planes is shown on the display or in the print of the screen. The screen display can be saved either in hard copy or electronically, and can be retrieved and referred to later to enable the patient to be scanned again with the same biplane image orientation.

It may be desirable to have the icon 400 graphically indicate the portion of the rotational circle 410 which corresponds to 0°–180°, and the portion which corresponds to 181°–359° in the numeric notation displayed below the icon. This may be done by using visibly distinguishable graphics for the lower and upper halves of the circle 410. For instance the lower half of the circle 410 could be displayed with a brighter or bolder line than the upper half, or could be dotted or dashed while the upper half is drawn with a solid line. Alternatively, the lower and upper halves could be differently colored, blue and green for instance, with the color of the numeric notation changed correspondingly with changes in the rotational angle of the right plane R.

FIG. 6 illustrates the display screen when operating in the "tilt" mode. In this mode the plane of the left image L is again fixed relative to the plane of the transducer array, and the right image R can be tilted from one side of the reference image to the other as if swinging from the common apex of the two images. In a constructed embodiment the two planes are always oriented 90° to each other in the lateral (rotational) spatial dimension. In a preferred embodiment the center line of the right sector image R always intersects the reference image, but at a line of the left sector which is selected by the user. An icon 600 indicates the relative orientation of the two image planes. In the icon 600 the small graphical sector 602 represents the fixed position of the left reference image. A cursor line 604 represents the right image viewed "edge-on" from the side. In this example the right image plane is tilted 30° from a nominal orientation in which the center lines of the two images are aligned, which is a 0° reference orientation. In the nominal (initial) orientation the cursor line is vertically oriented in the icon 600.

As an alternative to the icon 600, the cursor line 604 can be displayed over the reference image L. The user can manipulate a user control to change the tilt of the right plane R, or can drag the cursor line from one side of the image R to the other to change the tilt of the right plane. Cursor display types other than a line, such as dots or pointers, can also be used for cursor 604.

The tilt mode is particularly useful for conducting longitudinal studies of infarcts. Suppose that cardiac imaging of a patient reveals abnormal heart wall motion in the vicinity of the papillary muscle tips. With conventional 2D imaging, the clinician may try to image the infarcted wall by first acquiring an image of the papillary muscle in a long axis view of the heart, then rotating the probe ninety degrees to image the infarct location in a short axis view. However, if the probe (and hence the image plane) is not precisely rotated, the clinician can miss the infarct location. With the biplane tilt mode, the clinician can move the probe until the papillary muscle is shown in the reference image in a long axis view, then can tilt the cursor line 604 to point to or overlay the papillary muscle tips in the long axis reference image, thereby bringing the infarcted location into view in the tilted right image R in a short axis view. When the clinician wants to view the same section of the heart wall in a short axis view three or six months later in a longitudinal study, the process of imaging the papillary muscle in a long axis view in the left image, pointing the tilt cursor 604 in the same inclination, and viewing the infarcted region in a short axis view in the right image can be precisely repeated, thereby improving the diagnostic efficacy of the longitudinal study.

FIG. 7 shows two biplane images in the rotate mode. The icon between the two images in the center of the screen shows that the right image plane has been rotated ninety degrees from alignment with the left reference image plane. The marker dots are clearly visible in the icon and on the right sides of the apexes of the two sector images. For completeness of a cardiac study the EKG trace is also shown below the biplane images.

An advantage of the present invention is that since only two planes of a volumetric region are being imaged, acquisition of the two images can be done rapidly enough so that the two images can both be real-time ultrasonic images at a relatively high frame rate of display. A further advantage is that the ultrasound system need be only a conventional two dimensional imaging system. As FIG. 3 shows, the display subsystem for biplane imaging can be a conventional two dimensional image processing subsystem, which means that biplane imaging in accordance with the present invention can be done with the two dimensional ultrasound systems currently in the hands of clinicians. The scanner and display subsystem of FIG. 3 needs no unique 3D capabilities in order to produce the biplane image shown in FIG. 7.

The tilt and rotate modes can be combined, enabling a user to view biplane images which are both tilted and rotated relative to each other.

What is claimed is:

1. An ultrasonic diagnostic imaging system having a display screen and adapted to provide a diagnostic image display comprising:
    a first real time two dimensional image having an image plane orientation in relation to a transducer;
    a user control which can be continuously adjusted by a user;
    a second two dimensional real time image having a tilted or rotated plane orientation relative to the plane of the first two dimensional image which is continuously variable in real time in response to and during continuous manual manipulation of the user control; and
    an icon, displayed on the display screen concurrently with the first and second images, which depicts in real time the relative planar orientation of the first and second images as the user control is manipulated.

2. The ultrasonic diagnostic imaging system of claim 1, wherein the image display occupies an area of the display screen;
    wherein the first two dimensional image occupies a first portion of the area;
    wherein the second two dimensional image occupies a second portion of the area; and
    wherein the icon occupies a third portion of the area.

3. The ultrasonic diagnostic imaging system of claim 1, wherein the plane orientation of the second image can be selectively continuously tilted or rotated over a range of variation relative to the plane of the first image in response to manipulation of the user control.

4. The ultrasonic diagnostic imaging system of claim 1, wherein the image display occupies an area of the display screen;
    wherein the first two dimensional image occupies a first portion of the area;
    wherein the second two dimensional image occupies a second portion of the area; and
    wherein the icon is located in one of the first or second portions of the area.

5. The ultrasonic diagnostic imaging system of claim 1, wherein the icon further comprises a depiction of an image plane in relation to an identified side of the transducer.

6. The ultrasonic diagnostic imaging system of claim 1, wherein the image planes exhibit a given perspective in relation to the transducer; and
    wherein the icon depicts the image planes from the perspective of the transducer.

7. The ultrasonic diagnostic imaging system of claim 1, wherein the first two dimensional image has an image plane orientation which is fixed in relation to the transducer.

8. The ultrasonic diagnostic imaging system of claim 1, wherein the icon further comprises an indication of the angular orientation of the first image plane in relation to the second image plane.

9. The ultrasonic diagnostic imaging system of claim 8, wherein the indication of the angular orientation is a numerical indication.

10. The ultrasonic diagnostic imaging system of claim 1, wherein the icon further comprising a representation of the first image plane in the plane of the display screen, and a representation of the second image plane orthogonal to the plane of the display screen.

11. The ultrasonic diagnostic imaging system of claim 1, wherein at least one of the image planes exhibits a given limited range of variation; and
    wherein the icon further comprises a depiction of the range of variation of the orientation of at least one of the image planes.

12. An ultrasonic diagnostic imaging system comprising:
    an ultrasound probe which acts to scan two different image planes in real time, the image planes exhibiting a relative orientation to each other;
    a controller, coupled to the ultrasound probe, which controls the relative orientation of the image planes to be scanned by the probe;
    a user control, coupled to the controller, by which a user can vary the relative orientation of the image planes by manipulation of a single user control without manipulation of a guide figure with the user control; and
    a display, coupled to the probe, which simultaneously displays real time images of the two image planes and an indicator of the relative orientation of the image planes which varies in response to manipulation of the user control.

13. The ultrasonic diagnostic imaging system of claim 12, wherein the ultrasound probe acts to scan a first plane in a fixed predetermined orientation relative to the probe, and to scan a second plane in an orientation relative to the first plane which is user selectable,
    wherein the user control is variable to change the orientation of the second plane.

14. The ultrasonic diagnostic imaging system of claim 13, wherein the user control is variable to change the angle of rotation of the second plane in relation to the first plane,
    wherein the indicator indicates the angle of rotation of the second plane in relation to the first plane.

15. The ultrasonic diagnostic imaging system of claim 13, wherein the user control is variable to change the angle of inclination of the second plane in relation to the first plane,
    wherein the indicator indicates the angle of inclination of the second plane in relation to the first plane.

16. A method of displaying ultrasonic images of a volumetric region comprising:
    acquiring ultrasonic signals from at least two different planar areas of the volumetric region while omitting ultrasonic signals from planar area which are not to be imaged;
    processing the ultrasonic signals to develop images of the planar areas for which ultrasonic signals were acquired; and
    simultaneously displaying on an image display the images of the planar areas and an indicator of the spatial relationship of the planes of the planar areas,
    wherein acquiring further comprises acquiring ultrasonic signals from locations within the different planar areas in a time interleaved manner which is sufficiently rapid to display real-time images of the planar areas; and
    wherein simultaneously displaying further comprises simultaneously displaying on the image display real-time images of the planar areas.

17. The method of claim 16, further comprising varying the spatial relationship of the planar areas from which ultrasonic signals are acquired.

* * * * *